US009784705B2

(12) United States Patent
Miyamura et al.

(10) Patent No.: US 9,784,705 B2
(45) Date of Patent: Oct. 10, 2017

(54) MEASURING ELECTRODE AND MEASURING SYSTEM FOR CHEMICAL LIQUID

(71) Applicant: HORIBA, Ltd., Kyoto-shi, Kyoto (JP)

(72) Inventors: Kazuhiro Miyamura, Kyoto (JP); Koji Ueda, Kyoto (JP)

(73) Assignee: HORIBA, Ltd., Kyoto-shi, Kyoto (JP)

( * ) Notice: Subject to any disclaimer, the term of this patent is extended or adjusted under 35 U.S.C. 154(b) by 96 days.

(21) Appl. No.: 14/690,255

(22) Filed: Apr. 17, 2015

(65) Prior Publication Data

US 2015/0300972 A1    Oct. 22, 2015

(30) Foreign Application Priority Data

Apr. 18, 2014  (JP) ................. 2014-086106
Apr. 18, 2014  (JP) ................. 2014-086107
Apr. 18, 2014  (JP) ................. 2014-086108
Apr. 18, 2014  (JP) ................. 2014-086109

(51) Int. Cl.
    *G01N 27/26*       (2006.01)
    *G01N 27/30*       (2006.01)

(52) U.S. Cl.
    CPC ................. *G01N 27/301* (2013.01)

(58) Field of Classification Search
    CPC ........... G01N 27/4166; G01N 27/4167; G01N 27/301; G01N 27/302; G01N 27/333; G01N 27/4117; G01N 27/4035; G01N 27/26; B01L 2300/0877; B01L 2300/0668; B01J 2219/00653; B01J 2219/00722; B01J 2219/005
    See application file for complete search history.

(56) References Cited

U.S. PATENT DOCUMENTS

| 2,108,293 A | * | 2/1938 | Perley ............... G01N 27/4167 |
| | | | 204/409 |
| 3,658,679 A | | 4/1972 | Stansell et al. |
| 3,707,455 A | | 12/1972 | Derr et al. |

(Continued)

FOREIGN PATENT DOCUMENTS

| DE | 3010470 A1 | 10/1981 |
| JP | S55011521 U1 | 1/1980 |

(Continued)

OTHER PUBLICATIONS

Japan Patent Office, Office Action Issued in Japanese Application No. 2014-086106, dated Jun. 20, 2017, 3 pages.

(Continued)

*Primary Examiner* — Gurpreet Kaur
(74) *Attorney, Agent, or Firm* — Alleman Hall Creasman & Tuttle LLP

(57) ABSTRACT

A measuring electrode for chemical liquid in semiconductor process that measures a chemical liquid used for a semiconductor process comprises a first body having a first internal liquid chamber into which a first internal liquid is filled, and a flow tube for a part or all of which a responsive glass is used and that forms a flow channel where a chemical liquid as being a measuring object flows, wherein the flow tube is so arranged to penetrate the first body and the responsive glass makes contact with the first internal liquid in the first internal liquid chamber.

15 Claims, 6 Drawing Sheets

(56) References Cited

U.S. PATENT DOCUMENTS

| | | | | |
|---|---|---|---|---|
| 3,855,098 A * | 12/1974 | Fletcher, III | ......... | G01N 27/333 204/409 |
| 5,022,980 A | 6/1991 | Tanaka et al. | | |
| 6,162,337 A | 12/2000 | Iwamoto et al. | | |
| 8,673,627 B2 * | 3/2014 | Nobile | .............. | B01L 3/502761 257/253 |

FOREIGN PATENT DOCUMENTS

| | | |
|---|---|---|
| JP | S55135736 A | 10/1980 |
| JP | S57108151 U1 | 7/1982 |
| JP | S57122357 A | 7/1982 |
| JP | S58163867 U1 | 10/1983 |
| JP | 59183655 U | 12/1984 |
| JP | S59191655 U1 | 12/1984 |
| JP | S60159361 U1 | 10/1985 |
| JP | S60193455 U1 | 12/1985 |
| JP | S61068552 A | 4/1986 |
| JP | S61250548 A | 11/1986 |
| JP | S62105041 A | 5/1987 |
| JP | 62197758 A | 9/1987 |
| JP | H03048756 U1 | 5/1991 |
| JP | H10082759 A | 3/1998 |
| JP | 2002195974 A | 7/2002 |
| JP | 2006118907 A | 5/2006 |
| JP | 2013142591 A | 7/2013 |

OTHER PUBLICATIONS

Japan Patent Office, Office Action Issued in Japanese Application No. 2014-086107, dated Jun. 20, 2017, 3 pages.
Japan Patent Office, Office Action Issued in Japanese Application No. 2014-086108, dated Jun. 20, 2017, 4 pages.
Japan Patent Office, Office Action Issued in Japanese Application No. 2014-086109, dated Jun. 20, 2017, 3 pages.

* cited by examiner

MEASURING ELECTRODE AND MEASURING SYSTEM FOR CHEMICAL LIQUID

FIELD OF THE ART

This invention relates to a measuring electrode and a measuring system used for measuring a pH of a chemical liquid used for a cleaning solution in a semiconductor process.

BACKGROUND ART

A pH of a chemical liquid such as a cleaning solution used in a semiconductor process is measured in order to verify a cleaning effect of the chemical liquid. For example, a pH measuring device described in the patent document 1 samples and stores a chemical liquid used in a semiconductor manufacturing process and electrochemically measures a pH value by immersing a measuring electrode in the chemical liquid. The chemical liquid sampled by this measuring device is discarded after the measurement.

However, in accordance with this arrangement, there is a problem that a loss of the chemical liquid increases because the chemical liquid is stored in a measurement container and a considerable amount of the chemical liquid is required to be sampled for measurement.

PRIOR ART DOCUMENT

Patent Document

Patent document 1: Japanese Unexamined Patent Application Publication No. 2013-142591

DISCLOSURE OF THE INVENTION

Problems to be Solved by the Invention

The present claimed invention intends to solve all of the problems and a main object of this invention is to decrease a used amount of an objective liquid in measuring a pH of the objective liquid by the use of this kind of the measuring electrode.

Means to Solve the Problems

More specifically, a measuring electrode for chemical liquid used in semiconductor process in accordance with this invention is a measuring electrode for chemical liquid in semiconductor process to measure a chemical liquid used in a semiconductor process and comprises a body having an internal liquid chamber into which an internal liquid is filled and a flow tube for a part or all of which a responsive glass is used and that forms a flow channel where the chemical liquid as being a measuring object flows, and is characterized by that the flow tube is arranged in the body so as to make the responsive glass of the flow tube contact with the internal liquid in the internal liquid chamber.

In accordance with this arrangement, since an electrochemical measurement is conducted while the chemical liquid (hereinafter also called as the measuring liquid) as being the measuring object is flown in the flow tube without storing the chemical liquid in a storage, it is possible to reduce an amount of the chemical liquid that is used for the measurement and that is discarded after the measurement by making the flow tube thin or by limiting a flow rate of the chemical liquid that flows in the flow tube. As a result of this, it is possible to dramatically minimize a loss of the chemical liquid compared with the chemical liquid used by a conventional arrangement.

In addition, the measuring system in accordance with this invention comprises a chemical liquid flow control mechanism that controls the chemical liquid flowing in the flow tube, and the chemical liquid flow control mechanism halts the flow of the chemical liquid at a time of measuring the chemical liquid.

In accordance with this arrangement, since the flow of the chemical liquid is halted when, for example, an electromotive force of the chemical liquid is measured in the electrochemical measurement, it is possible to further lessen the used amount of the chemical liquid so that the loss of the chemical liquid can be decreased. In addition, also in case of measuring the electromotive force by halting the flow of the chemical liquid, if the flow tube is thin, the measurement is not affected by a convection current of the chemical liquid so that the measurement accuracy is improved. Furthermore, since the measurement of the electromotive force is conducted in a state that the flow of the chemical liquid is halted, it is possible to avoid an influence on the measurement value due to the flow of the chemical liquid.

The measuring electrode or the measuring system for chemical liquid in semiconductor process in accordance with this invention is characterized by that the flow tube is in a capillary shape.

In accordance with this arrangement, since the flow tube is formed further thinner, it is possible to furthermore reduce the amount of the chemical liquid used for the measurement so that the loss of the chemical liquid can be decreased.

In addition to the above-mentioned invention group 1, this specification also describes following invention group 2, invention group 3 and invention group 4.

(Invention Group 2)

The invention group 2 relates to a measuring system used in an electrochemical measurement such as a pH measurement, and the measuring liquid is not limited to the chemical liquid used for semiconductor process.

A background art and a problem of the invention group 2 are as follows.

An electrochemical measuring device including a pH measuring device by the use of a glass electrode method comprises a measuring electrode and a reference electrode. Since the internal liquid of the reference electrode is diluted when the measuring liquid as being the measuring object makes contact with the internal liquid of the reference electrode, it is necessary to replenish the internal liquid of the reference electrode in order to keep the measurement accuracy. Then, in case that the electrochemical measuring device is used for a long period of time, for example, about 6 months, it is necessary to replenish the internal liquid of the reference electrode during this period of time in order to keep the measurement accuracy. If it is possible to decrease the replenishing amount of the internal liquid, labor for maintenance of the device can be saved.

There are various arrangements as the reference electrode. For example, the reference electrode shown in FIG. 2 in the patent document (Utility Model Publication of Application No. 59-183655) has an arrangement wherein an internal electrode of the reference electrode extends upward from the bottom end of the reference electrode, the measuring liquid flows in an upper space of the reference electrode, a liquid junction is provided on an interface between the measuring liquid and the internal liquid, and an internal liquid replenishing port is provided above the upper end of the internal electrode.

With the arrangement of the reference electrode described in this patent document, since the internal liquid leaks through the liquid junction locating in the upper part of the reference electrode, a replenishing mechanism to replenish the internal liquid is necessary to keep the measurement accuracy in case of a long term use assumed by this invention. However, if the internal liquid is replenished on a constant basis, there is a problem that the replenishing amount of the internal liquid increases.

The invention group 2 in accordance with the above-mentioned measuring system is to solve the above-mentioned problem and a main object is to reduce the replenishing amount of the internal liquid, to keep the measurement accuracy and to save the labor for maintenance of the device in the long term use of this measuring system.

A main invention among the invention group 2 invented to solve this problem is a measuring system that comprises a body that has an internal liquid chamber into which an internal liquid whose specific gravity is bigger than that of the measuring liquid as being an measuring object is filled and that is so configured that the internal liquid makes contact with the measuring liquid flowing above the internal liquid through the liquid junction arranged at the upper end part of the internal liquid chamber, a reference electrode that comprises an internal electrode arranged to contact the internal liquid in the internal liquid chamber and an internal liquid replenishing mechanism that replenishes the internal liquid into the internal liquid chamber, and is characterized by that the internal liquid replenishing mechanism replenishes the internal liquid by a predetermined amount intermittently.

In accordance with this arrangement, since the specific gravity of the internal liquid is bigger than that of the measuring liquid and the amount of the measuring liquid that flows into the internal liquid side through the liquid junction arranged in the upper end part of the internal liquid chamber is due to diffusion alone, it is possible to reduce the measuring liquid flowing in because of diffusion and to reduce the amount of the internal liquid that flows out. In addition, since the specific gravity of the internal liquid is bigger than that of the measuring liquid, a part of the internal liquid whose concentration is diluted because the measuring liquid flows in locates in the upper part of the internal liquid chamber. The internal electrode is arranged to extend upward from the bottom end part of the internal liquid chamber, even though the internal liquid is intermittently replenished by means of the internal liquid replenishing mechanism, the diluted internal liquid can be replaced by the replenished internal liquid in time before the diluted internal liquid reaches the internal electrode. As a result of this, the concentration of the internal liquid around the internal electrode can be kept. As mentioned above, since the internal liquid is intermittently replenished, it is possible to make the amount of the internal liquid small to keep the accuracy of the electric potential measurement.

In addition, the invention group 2 also includes the invention of the measuring system wherein the internal liquid chamber of the reference electrode is so formed that a cross section of the internal liquid chamber at a position locating above the upper end of the internal electrode and separated from the liquid junction by the predetermined distance is smaller than a cross section of the internal liquid chamber locating below the position.

In accordance with this arrangement, since the cross section of the internal liquid chamber at the position separated from the liquid junction by the predetermined distance is smaller than the cross section of the internal liquid chamber locating below the position, it is possible to reduce a volume of the internal liquid chamber at a part separated from the liquid junction by the predetermined distance compared with a case wherein the cross section is constant in any position of the internal liquid chamber. Since the speed of the measuring liquid flowing in a side of the internal liquid due to diffusion is the same, if the volume of the internal liquid chamber separated from the liquid junction by the predetermined distance is smaller, in case that the diluted amount of the internal liquid due to diffusion of the measuring liquid is to be replaced, it is possible to reduce a replacing amount of the internal liquid. As a result of this, the amount of the internal liquid to be replaced becomes small so that the amount of the internal liquid to be replenished at a time by the internal liquid replenishing mechanism can be further decreased.

In addition, the invention group 2 also includes the measuring system wherein the volume of the internal liquid chamber of the reference electrode from the liquid junction to the position separated from the liquid junction by the predetermined distance is set to be smaller than an amount of the internal liquid replenished at a time by the internal liquid replenishing mechanism.

In accordance with this arrangement, in case that the internal liquid is diluted because the measuring liquid diffuses between the liquid junction and the position separated from the liquid junction by the predetermined distance, since an amount of the internal liquid that is more than an amount corresponding to the diluted amount of the internal liquid is replenished by the internal liquid replenishing mechanism, the diluted part of the internal liquid can be pushed out from the liquid junction and replaced by the internal liquid securely.

(Invention Group 3)

The invention group 3 relates to a reference electrode used in an electrochemical measurement device such as a pH measurement device, and the measuring object is not limited to the chemical liquid used for semiconductor process.

A background art and a problem of the invention group 3 are as follows.

An electrochemical measuring device including a pH measuring device by the use of a glass electrode method comprises a measuring electrode and a reference electrode. Since the internal liquid of the reference electrode is diluted when the measuring liquid as being the measuring object makes contact with the internal liquid of the reference electrode, it is necessary to replenish the internal liquid of the reference electrode in order to keep the measurement accuracy. Then, in case that the electrochemical measuring device is used for a long period of time, for example, about 6 months, it is necessary to replenish the internal liquid of the reference electrode during this period of time in order to keep the measurement accuracy. If it is possible to decrease the replenishing amount of the internal liquid, labor for maintenance of the device can be saved.

There are various arrangements as the reference electrode. For example, the reference electrode shown in FIG. 2 in the patent document (Utility Model Publication of Application No. 59-183655) has an arrangement wherein an internal electrode of the reference electrode extends upward from the bottom end of the reference electrode, the measuring liquid flows in an upper space of the reference electrode, a liquid junction is provided on an interface between the measuring liquid and the internal liquid, and an internal liquid replenishing port is provided above the upper end of the internal electrode.

With the arrangement of the reference electrode described in this patent document, since the internal liquid leaks through the liquid junction locating in the upper part of the reference electrode, a replenishing mechanism to replenish the internal liquid is necessary to keep the measurement accuracy in case of a long term use assumed by this invention. However, since the internal liquid replenishing port is provided above the upper end of the internal electrode and near the liquid junction, even though the internal liquid is replenished from the internal liquid replenishing port, the replenished internal liquid flows out from the liquid junction. Then in order to replace the internal liquid around the internal electrode, there is a problem that a considerable amount of the internal liquid is required to be replenished.

The invention group 3 in accordance with the above-mentioned measuring system is to solve the above-mentioned problem and a main object is to reduce the replenishing amount of the internal liquid, to keep the measurement accuracy and to save the labor for maintenance of the device in the long term use of this measuring system using this reference electrode.

A main invention among the invention group 3 invented to solve this problem is a reference electrode that comprises a body that has an internal liquid chamber into which an internal liquid is filled and that is so configured that the internal liquid makes contact with a measuring liquid as being a measuring object flowing above the internal liquid through a liquid junction arranged at an upper end part of the internal liquid chamber and an internal electrode that is arranged so as to contact the internal liquid in the internal liquid chamber, and is characterized by that a replenishing port to replenish the internal liquid into the internal liquid chamber is arranged below the upper end part of the internal electrode.

In accordance with this arrangement, since the internal liquid is replenished from the replenishing port arranged below the upper end part of the internal electrode, it is possible to replace the liquid around the internal electrode by the replenished internal liquid so that the measurement accuracy can be kept. In this case, since the internal liquid pushes up and replaces the part where the internal liquid is diluted due to diffusion of the measuring liquid from the liquid junction, all needed is just to replenish an amount of the internal liquid corresponding to an amount of the diluted part so that it is possible to economize and reduce the replenishing amount of the internal liquid.

In addition, the invention group 3 also includes the invention of the reference electrode that is characterized by that a specific gravity of the internal liquid is bigger than a specific gravity of the measuring liquid.

In accordance with this arrangement, since the specific gravity of the internal liquid is bigger than that of the measuring liquid and the amount of the measuring liquid that flows into the internal liquid side through the liquid junction arranged in the upper end part of the internal liquid chamber is due to diffusion alone, it is possible to reduce the measuring liquid flowing in because of diffusion and to reduce the amount of the internal liquid that flows out. In addition, since the specific gravity of the internal liquid is bigger than that of the measuring liquid, a part of the internal liquid whose concentration is diluted because the measuring liquid flows in locates upper part of the internal liquid chamber. Since the internal electrode is arranged to extend upward from the bottom end part of the internal liquid chamber, the diluted part of the internal liquid can be securely pushed up and the liquid around the internal electrode can be replaced by the internal liquid replenished from the replenishing port locating below the upper end part of the internal electrode. As a result of this, it is possible to keep the measurement accuracy. With this arrangement, the replenishing amount of the internal liquid can be economized and reduced.

In addition, the invention group 3 also includes the invention of the reference electrode characterized by that the internal liquid chamber is so formed that a cross section of the internal liquid chamber at a position locating above the upper end of the internal electrode and separated from the liquid junction by the predetermined distance is smaller than a cross section of the internal liquid chamber locating below the position.

In accordance with this arrangement, since the cross section of the internal liquid chamber at the position separated from the liquid junction by the predetermined distance is smaller than the cross section of the internal liquid chamber locating below the position, it is possible to reduce a volume of a part of the internal liquid chamber from the liquid junction to the position separated from the liquid junction by the predetermined distance compared with a case wherein the cross section is constant in every position of the internal liquid chamber. Since the speed of the measuring liquid flowing in the side of the internal liquid due to diffusion is the same, in case that the diluted amount of the internal liquid due to diffusion of the measuring liquid is to be replaced, the volume of the diluted part is small so that it is possible to reduce a replacing amount of the internal liquid. As a result of this, the replenishing amount of the internal liquid can be further decreased.

In addition, the invention group 3 also includes an invention of the reference electrode that is characterized by that a volume of a part of the internal liquid chamber from the liquid junction to a position separated from the liquid junction by the predetermined distance is set to be smaller than an amount of the internal liquid replenished at a time from the replenishing port.

In accordance with this arrangement, in case that the internal liquid is diluted due to the measuring liquid that diffuses between the liquid junction and the position separated from the liquid junction by the predetermined distance, since the internal liquid is replenished by an amount that is more than an amount corresponding to the amount of the diluted internal liquid, it is possible to push up the diluted internal liquid from the liquid junction and to replace the diluted internal liquid securely by the replenished internal liquid.

(Invention Group 4)

The invention group 4 relates to an electrode device comprising a measuring electrode and a reference electrode used for a pH measurement device or the like, and the measuring object is not limited to the chemical liquid used for semiconductor process.

A background art and a problem of the invention group 4 are as follows.

There is a case that a flow injection analysis to measure a pH by obtaining a part of the flowing measuring liquid one after another or continuously uses not a polarograph device as shown in the patent document (Japanese Unexamined Patent Application Publication No. 62-197758) but a grass electrode method. If the pH measurement by the glass electrode method uses the art as described in this invention group 1, there might be a case that the internal liquid is contaminated by the measuring liquid. As a result of this, the measurement accuracy is influenced.

A concrete explanation will follow. For example, an example of a configuration (not a well-known conventional example) shown in FIG. 6 has such a configuration that a pair of internal liquid chambers that house an internal liquid and an internal electrode are arranged in a body 202 in a block shape, and one of the pair is a measuring electrode 204 and the other is a reference electrode 206.

A flow tube 208 formed by a responsive glass fits into a body 202 of the measuring electrode 204 in a state of penetrating the internal liquid chamber 204a of the measuring electrode 204, a through hole 210 that communicates with the flow tube 208 is provided for the body 202 of the reference electrode 206 and the through hole 210 is in communication with the internal liquid chamber 206a of the reference electrode 206 through a liquid junction 212.

A measuring liquid 216 flows in a measuring liquid flow channel 214 formed by the flow tube 208 and the through hole 210 and a pH of the measuring liquid 216 is measured by the use of the measuring electrode 204 and the reference electrode 206.

A part where the flow tube 208 and the through hole 210 are connected is surrounded and covered by an adhesive or a connecting member 218 such as an O ring or the like so as to connect the flow tube 208 and the through hole 210 liquid-tightly.

However, in accordance with this arrangement, a measurement error might be generated in the reference electrode 206 because of the contamination when the internal liquid 204b of the measuring electrode 204 enters the measuring liquid flow channel 214 through a gap between the flow tube 208 and the connecting member 218 or a gap between the body 202 and the connecting member 218 as shown by a wavy line in an enlarged view of the connecting part due to aged deterioration of the connecting member 218 or a contingent careless mistake at a time of initial assembly.

The invention group 4 in accordance with the electrode device is to solve all of the problems and a main object is to prevent contamination of the measuring liquid so as to keep the measurement accuracy at a time of measuring the pH by the electrochemical measurement.

A main invention among the invention group 4 invented to solve this problem is an electrode device that comprises a measuring electrode and a reference electrode wherein the measuring electrode comprises a first body that forms a first internal liquid chamber that houses a first internal liquid and a first internal electrode and a flow tube for a part or all of which a responsive glass is used and that is inserted into the first body so as to pass the first internal liquid chamber, wherein the measuring liquid as being a measuring object that flows in the flow tube is supplied to the reference electrode, and is characterized by that an output end side of the flow tube connected to the reference electrode projects from the first body and an area of the projecting part that extends over the predetermined length is exposed to a space.

In accordance with this arrangement, even though the first internal liquid leaks from the gap between the first body and the flow tube, since a space exposed area provided in the output end side of the flow tube blocks the first internal liquid from being transmitted to the reference electrode, it is possible to prevent the internal liquid (the first internal liquid) of the measuring electrode from mixing into the flow channel where the measuring liquid flows in the reference electrode securely so that the measurement accuracy of the electric potential can be kept.

In order to hold the projecting part of the flow tube with ease a sub-body that is arranged separately from the first body is further provided and the space is arranged between the first body and the sub-body. It is preferable that a part of the flow tube bridges the space.

In order to securely hold the flow tube and to prevent the flow tube from being bent or broken because a contingent bending force is applied, it is preferable to further comprise a connecting body that connects the first body and the sub-body.

It is further preferable that a connecting port connected with the reference electrode is formed on the sub-body.

As a concrete embodiment of a reference electrode that is useful for downsizing or for reducing a consumed amount of the measuring liquid represented is an arrangement wherein the reference electrode comprise a second internal liquid chamber into which a second internal liquid is filled and a second body that forms a second flow channel where the measuring liquid flows, and the measuring liquid in the second flow channel makes contact with the second internal liquid in the second internal liquid chamber through a liquid junction.

In order to hold the projecting part of the flow tube with ease, a second sub-body that is arranged separately from the second body is further provided and the space is arranged between the second body and the second sub-body. It is preferable that a part of the flow tube bridges over the space.

Furthermore, in order to hold the flow tube securely and to prevent the flow tube from being bent or broken because a contingent bending force is applied, it is preferable that the reference electrode comprises the second connecting body to connect the second body and the second sub-body.

In addition, it is preferable that the flow tube is formed by connecting a plurality of flow tube elements.

As a concrete embodiment of connecting a plurality of flow tube elements, it is preferable that on one end part of the other flow tube element fits over one end part of one flow tube element and a part where each flow tube element fits is tightened by a ring-shape tightening member.

More concretely, the tightening member is a ferrule and a fitting member that is arranged to make an abutting contact with the ferrule and to fits into the first body connects each of the flow tube elements by the ferrule that presses the part where the flow tube elements fit each other.

In addition, when the first internal liquid leaks from a gap between the first body and the flow tube, it is preferable that a part of the space is open in order to discharge the first internal liquid from the space without storing the first internal liquid.

BEST MODES OF EMBODYING THE INVENTION

On embodiment of this invention will be explained with reference to drawings.

First Embodiment

Figure 1:
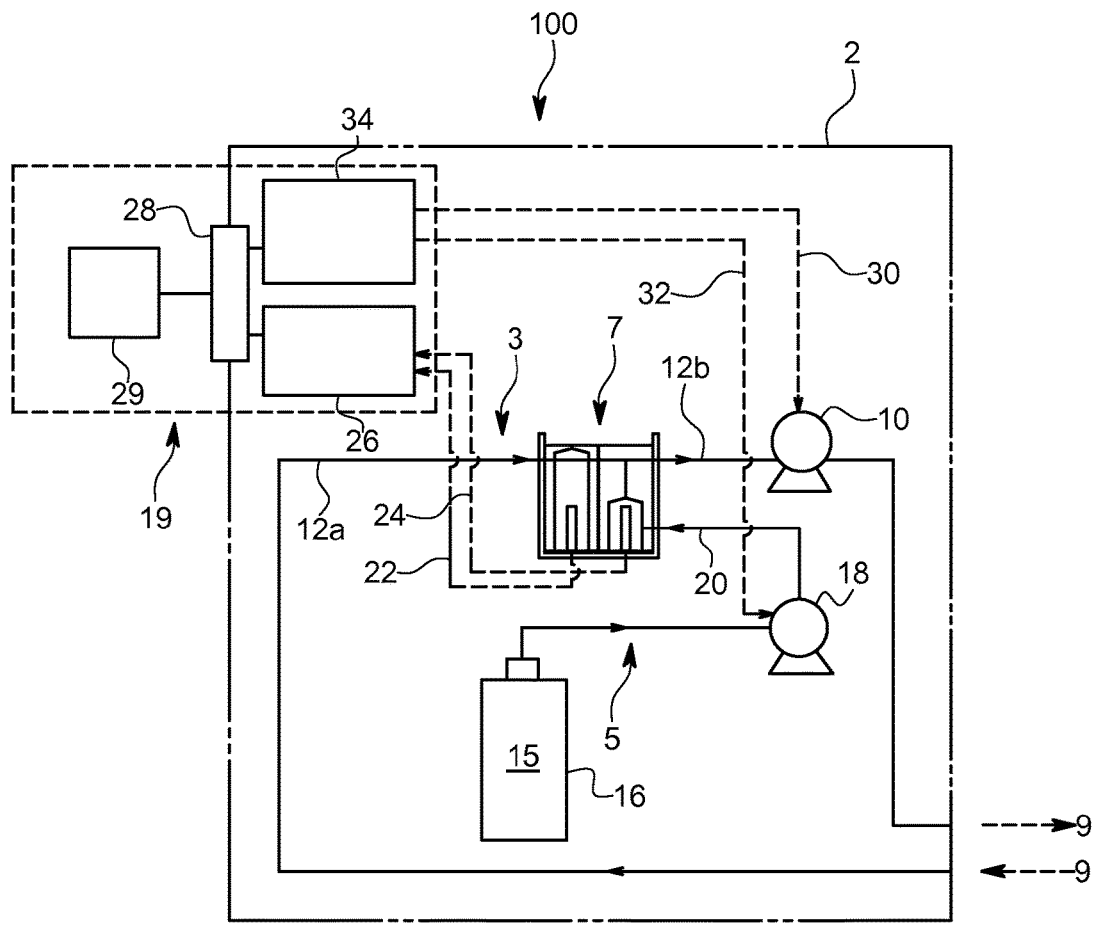
FIG. 1 is a general schematic view of a measuring system in accordance with one embodiment of this invention.

FIG. 1 shows a measuring system 100 in accordance with this embodiment.

The measuring system 100 is to continuously monitor a concentration of a hydrogen ion of a chemical liquid (hereinafter also called as "a measuring liquid") used in a semiconductor manufacturing process such as, for example, cleaning of a wiring process, Cu plating, and CMP (chemical mechanical polishing), and comprises an electrode device 7 to measure a pH of the measuring liquid 9, a measuring liquid flow control mechanism 3 to flow the measuring liquid 9 in the electrode device 7, an internal liquid replenishing mechanism 5 to replenish an internal liquid (hereinafter also called as "a second internal liquid") such as a KCL solution to the electrode device 7, and an information processing/control mechanism 19 to be connected to the electrode device 7, the measuring liquid flow control mechanism 3 and the internal liquid replenishing mechanism 5 and to transfer measurement data or a control command signal therebetween.

The measuring system 100 can also measure, for example, an ionic concentration of sodium and an ionic concentration of potassium, and a gas concentration of carbon dioxide (pCO2) and a gas concentration of oxygen (pO2) in addition to a concentration of a hydrogen ion.

Figure 2:
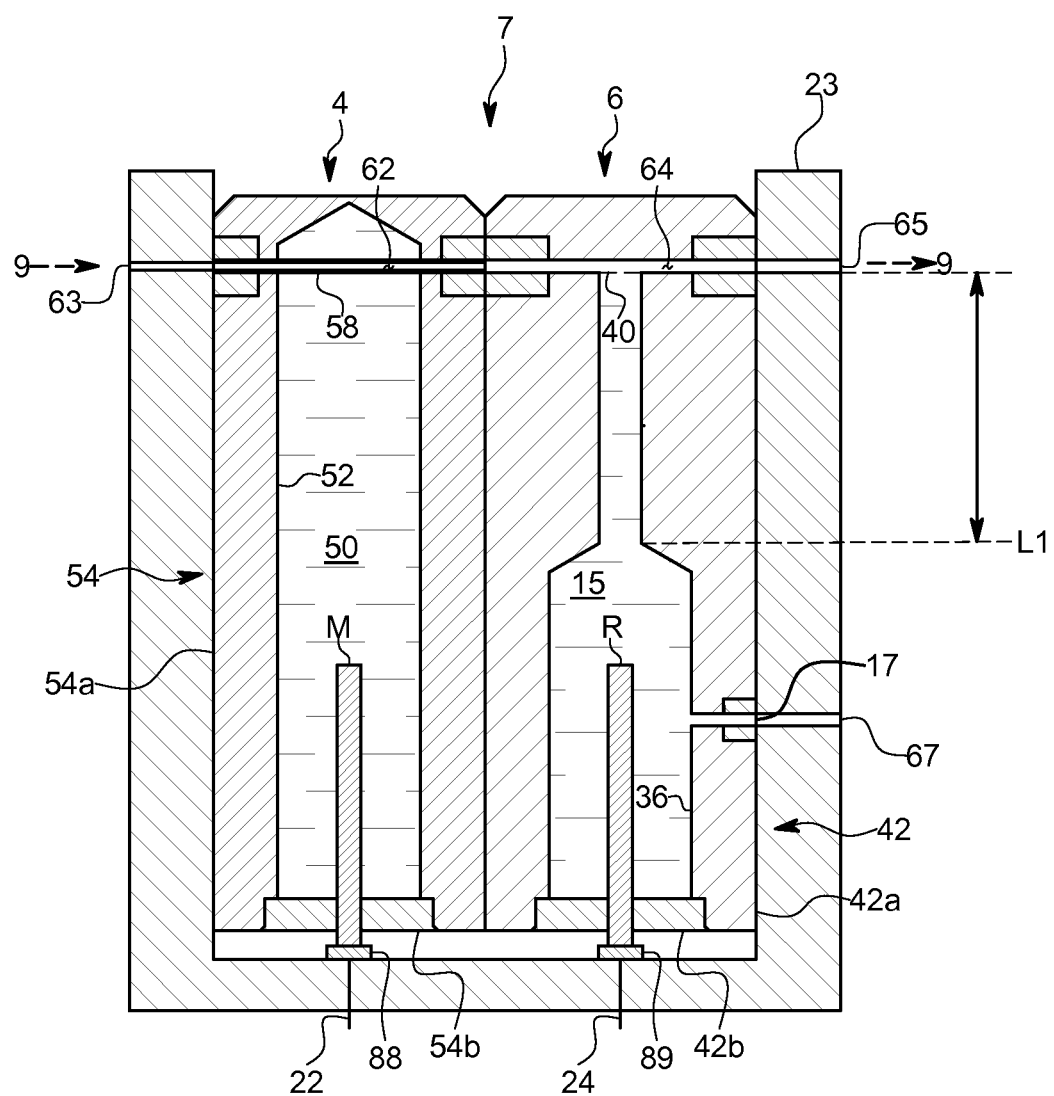
FIG. 2 is a schematic view of an electrode device in this embodiment.

The electrode device 7 comprises, as shown in FIG. 2, a measuring electrode 4 for chemical liquid in semiconductor process (hereinafter also called just as the measuring electrode 4), a reference electrode 6 and a frame body 23 that houses the measuring electrode 4 and the reference electrode 6.

The measuring electrode 4 comprises a body (a body described in claim 1, and hereinafter called as "a first body 54") having an internal liquid chamber (an internal liquid chamber described in claim 1, and hereinafter called as "a first internal liquid chamber 52") into which a predetermined internal liquid (an internal liquid described in claim 1, and hereinafter called as "a first internal liquid 50") such as a pH buffer solution and an internal electrode (M) mounted to extend upward from a lower part of the first body 54 in the internal liquid chamber 52.

The first body 54 is made of a material such as PVC (polyvinyl chloride), PP (polypropylene) and PVDF (polyvinylidene fluoride), and comprises a main member 54a in a vertically extending rectangular cylindrical shape whose top surface is closed and whose bottom surface is open and a cap body 54b that closes the bottom surface opening of the main member 54a. The first internal liquid chamber 52 formed inside of the first body 54 has a constant cross-sectional shape (for example, a cylindrical shape) from, for example, the bottom end to a predetermined height and only the upper end part is in a conical shape whose cross section gradually narrows toward an upper part.

The internal electrode (M) comprises, for example, a silver/silver chloride electrode, and is mounted with a bottom end part of the internal electrode (M) penetrating the cap body 54b and stands from the cap body 54b extending upward in the first internal liquid chamber 52. In addition, a point of contact is provided on the bottom end of the internal electrode (M) so as to make it possible to take an electric current (a voltage) signal out to the outside. The internal electrode (M) is not limited to an arrangement wherein the bottom end part extends from the cap body 54b, and may extend from a side surface of the main member 54a upward obliquely or in a shape of, for example, an "L" character in the first internal liquid chamber 52.

Furthermore, in this embodiment, the electrode device 7 comprises a flow tube 58 where the measuring liquid 9 flows.

Whole of the flow tube 58 is formed by a responsive glass that responds to the hydrogen ion and forms a first flow channel 62 where the chemical liquid flows. The responsive glass contains a predetermined amount of scandium. A shape of the flow tube 58 is capillary, in other words, a length of the flow tube 58 is sufficiently long relative to an inner diameter of the flow tube 58, and the flow tube 58 is extremely thin, for example, the inner diameter is about 0.1 mm to 2 mm, preferably about 0.5 mm to 1 mm. In addition, a thickness of the flow tube 58 is about 0.1 mm to 1 mm, and preferably about 0.2 mm. If the thickness is about 0.2 mm, the responsive glass has high responsiveness. Furthermore, an outer diameter of the flow tube 58 is about 0.3 mm to 4 mm, and preferably about 1 mm to 2 mm.

The flow tube 58 is arranged to horizontally penetrate the first body 54 at the upper end part of the first body 54 and to be immersed in the first internal liquid 50 in the first internal liquid chamber 52. More concretely, the flow tube 58 is arranged to penetrate a part of the first internal liquid chamber 52 whose cross section is constant and that locates above the upper end part of the internal electrode (M).

The responsive glass may be used for a part of the flow tube 58 that is immersed into the first internal liquid 50.

Next, the reference electrode 6 will be explained by the use of FIG. 2.

The reference electrode 6 comprises a second body 42 (a body of the reference electrode described in claim 1) having an internal liquid chamber (an internal liquid chamber of the reference electrode described in claim 1, and hereinafter called as "a second internal liquid chamber") into which a second internal liquid 15 is filled, an internal electrode (R) mounted to extend upward from a lower part of the second body 42 in a second internal liquid chamber 36 and a replenishing port 17 that is formed in the second body 42 and in communication with the second internal liquid chamber 36 to replenish the second internal liquid 15.

Similar to the first body 54 of the measuring electrode 4, the second body 42 is made of a material such as PVC, and comprises a main member 42a in a vertically extending rectangular cylindrical shape whose top surface is closed and whose bottom surface is open and a cap body 42b that closes the bottom surface opening of the main member 42a.

The second internal liquid chamber 36 arranged in the second body 42 is formed to have a cross section of a position both above the upper end part of the internal electrode (R) and in a predetermined distance (L1) downward from a liquid junction 40 that is smaller than a cross section of a position below the position of the predetermined distance (L1). Furthermore, a volume of the second internal liquid chamber 36 from the liquid junction 40 to the predetermined distance (L1) is set to be smaller than an amount of the second internal liquid 15 replenished at a time from the replenishing port 17.

A cross section (a cross section is a circle in this embodiment) of the position between the liquid junction 40 and the predetermined distance (L1) may be constant or may be varied as far as the cross section is smaller than a cross section of a part below the predetermined position (L1). The cross section of the part below the predetermined distance (L1) may be similarly constant or varied.

Furthermore, in this embodiment, the second flow channel 64 where the measuring liquid 9 flows is formed in the second body 42. The second flow channel 64 is formed horizontally at the upper end part of the second body 42, and is so configured that the second internal liquid 15 contacts the measuring liquid 9 flowing in the second flow channel 64 through the liquid junction 40 formed by minute bores arranged at the upper end part of the second internal liquid chamber 36.

The internal electrode (R) comprises, for example, a silver/silver chloride electrode, and is mounted with a bottom end part of the internal electrode (R) penetrating the cap body 42b and stands from the cap body 42b extending upward in the second internal liquid chamber 36. In addition, a point of contact is provided on the bottom end of the internal electrode (R) so as to make it possible to take an electric current (a voltage) signal out to the outside. The internal electrode (R) is not limited to an arrangement wherein the bottom end part extends from the cap body 42b, and may extend from a side surface of the main member 42a upward obliquely or in a shape of, for example, an "L" character in the second internal liquid chamber 36.

The replenishing port 17 is arranged at a point a little lower than the upper end part of the internal electrode (R) in this embodiment, however, it may be appropriately varied such that the replenishing port 17 is arranged at a position further downward, for example, at a position which makes it possible to replenish the second internal liquid 15 from a direction of a bottom part of the second internal liquid chamber 36, or the replenishing port 17 is arranged at a position of a center or an upper part of the internal electrode (R).

Next, the frame body 23 will be explained by the use of FIG. 2. The frame body 23 is made of a material such as a resin or a metal in a square box shape whose upper part opens, and the measuring electrode 4 and the reference electrode 6 are fittingly inserted from upward into the frame body 23.

A contact point 88 with which the bottom end part of the internal electrode (M) makes contact and a contact point 89 with which the bottom end part of the internal electrode (R) makes contact are arranged on the bottom plate of the frame body 23.

In addition, a flow-in hole 63 to introduce the measuring liquid 9 into the flow tube 58 that forms the first flow channel 62 is formed on one side plate of the frame body 23 that makes contact with the measuring electrode 4, and a flow-out hole 65 to discharge the measuring liquid 9 that flows in the second flow channel 64 is formed on the other side plate of the frame body 23. Furthermore, a flow-in hole 67 to introduce the second internal liquid 15 to the replenishing port 17 is also formed on the other side plate.

As mentioned above, the electrode device 7 comprises the measuring electrode 4, the reference electrode 6 and the frame body 23, and the measuring electrode 4 and the reference electrode 6 are housed in the frame body 23 in a state that the flow-in hole 63, the first flow channel 62, the second flow channel 64 and flow-out hole 65 communicate each other and furthermore the replenishing port 17 and the flow-in hole 67 communicate each other. The measuring electrode 4 and the reference electrode 6 are fixed by means of, for example, a screw, not shown in drawings, in a state of being pushed each other. With this arrangement, the first flow channel 62 and the second flow channel 64 tightly attach each other so as not to leak the measuring liquid 9 from a space between the first flow channel 62 and the second flow channel 64. In order to improve adherence, an O-ring may be provided between the first flow channel 62 and the second flow channel 64. In addition, the flow tube 58 is fixed to a part where the flow tube 58 penetrates the first body 54 in the measuring electrode 4 by means of an adhesive or the like and the part is sealed so as not to leak the first internal liquid 50 from the first internal liquid chamber 52.

Next, the measuring liquid flow control mechanism 3 comprises a flow-in pipe 12a to introduce the measuring liquid 9 into the electrode device 7, a flow-out pipe 12b to flow the measuring liquid 9 flowing out through the electrode device 7 and a flow pump 10 that is arranged at a predetermined position of the flow-in pipe 12a or the flow-out pipe 12b to introduce and discharge the measuring liquid 9, and controls the flow of the measuring liquid 9.

The flow-in pipe 12a is so arranged that a distal end part of the flow-in pipe 12a is inserted into the flow-in hole 63 of the frame body 23 and connected with the flow tube 58 of the measuring electrode 4 and the measuring liquid 9 is injected from a proximal end part of the flow-in pipe 12a. The distal end part of the flow-in pipe 12a and the flow tube 58 of the measuring electrode 4 are connected so as to be tightly attached each other by an adhesive or the like so as to introduce the measuring liquid 9 into the measuring electrode 4 without leakage.

The flow-out pipe 12b is so arranged that a proximal end part of the flow-out pipe 12b is inserted into the flow-out hole 65 of the frame body 23 and connected with the second flow channel 64 of the reference electrode 6 and the measuring liquid 9 is discharged from a distal end part of the flow-out pipe 12b. The proximal end part of the flow-out pipe 12b and the second flow channel 64 of the reference electrode 6 are connected so as to be tightly attached each other by an adhesive or the like so as to discharge the chemical liquid 9 from the second flow channel 64 without leakage.

In addition, the flow pump 10 is arranged at a predetermined position of the flow-in pipe 12a or the flow-out pipe 12b, for example, between the proximal end part and the distal end part of the flow-out pipe 12b. Due to the operation of the flow pump 10, the measuring liquid 9 flows in the flow-in pipe 12a, the measuring electrode 4 and the reference electrode 6 successively and flows in the flow-out pipe 12b and then is discharged to the outside of the measuring system 100.

Next, the internal liquid replenishing mechanism 5 will be explained by the use of FIG. 1 and FIG. 2. The internal liquid replenishing mechanism 5 comprises a container 16 in which the second internal liquid 15 is stored, a replenishing pipe 20 that connects the container 16 and the reference electrode 6 and that replenishes the second internal liquid 15 to the reference electrode 6 and a replenishing pump 18 that is arranged at a predetermined position of the replenishing pipe 20 and that flows the second internal liquid 15. The replenishing pipe 20 is so configured that a proximal end part is connected to the container 16 and a distal end part is inserted into the flow-in hole 67 of the frame body 23 and connected to the replenishing port 17. The distal end part of the replenishing pipe 20 and the replenishing port 17 of the reference electrode 6 are connected so as to be tightly attached each other by an adhesive or the like so as to flow the second internal liquid 15 into the second internal liquid chamber 36 without leakage. In order to improve adhesiveness, an O-ring or the like may be provided between the replenishing pipe 20 and the replenishing port 17.

The replenishing pump 18 is arranged between the proximal end part and the distal end part of the replenishing pipe 20. Due to the operation of this replenishing pump 18, the second internal liquid 15 from the container 16 flows in the replenishing pipe 20 and passes the replenishing port 17 and then is replenished to the reference electrode 6.

Next, the information processing/control mechanism 19 will be explained by the use of FIG. 1 and FIG. 2. The information processing/control mechanism 19 comprises a potentiometer 26 to calculate a pH value of the measuring liquid 9 measured by the electrode device 7, a driver circuit 34 comprising a circuit to operate the flow pump 10 and the replenishing pump 18 and a control device 29 that processes the information obtained by the potentiometer 26 and that comprises a computer to output an operation signal to the driver circuit 34 and a display. In this embodiment, the control device 29 is arranged outside of a casing 2. The information processing/control mechanism 19 itself may be arranged outside of the casing 2.

The potentiometer 26 is electrically connected to the internal electrode (M) of the measuring electrode 4 and the internal electrode (R) of the reference electrode 6 in the electrode device 7 by a wire 22 of the internal electrode (M) and a wire 24 of the internal electrode (R) through the contact points 88, 89. With this arrangement, a potential difference between the internal electrode (M) and the internal electrode (R) is measured by means of the potentiometer 26 based on each electric potential detected by the internal electrode (M) and the internal electrode (R). The potentiometer 26 is electrically connected to the control device 29 through an external connecting terminal 28, and the control device 29 calculates the pH value of the measuring liquid 9 based on an output value of the potentiometer 26 by means of the computer and displays the calculated value on the display. The calculated pH value is stored in a memory media of the computer and can be displayed when necessary.

The driver circuit 34 is electrically connected to the flow pump 10 and the replenishing pump 18 through wires 30, 32, and the driver circuit 34 is electrically connected to the control device 29 through the external connecting terminal 28. The driver circuit 34 controls operation or halt of the flow pump 10 and the replenishing pump 18 based on the signal from the computer of the control device 29 and adjusts a timing and an amount of the measuring liquid 9 flowing in the electrode device 7. In addition, the amount of the second internal liquid 15 to replenish or the timing to replenish the second internal liquid 15 is controlled so as to make it possible to continuously operate the measuring system 100 for several months, for example, about 4 months to 8 months.

Figure 3:
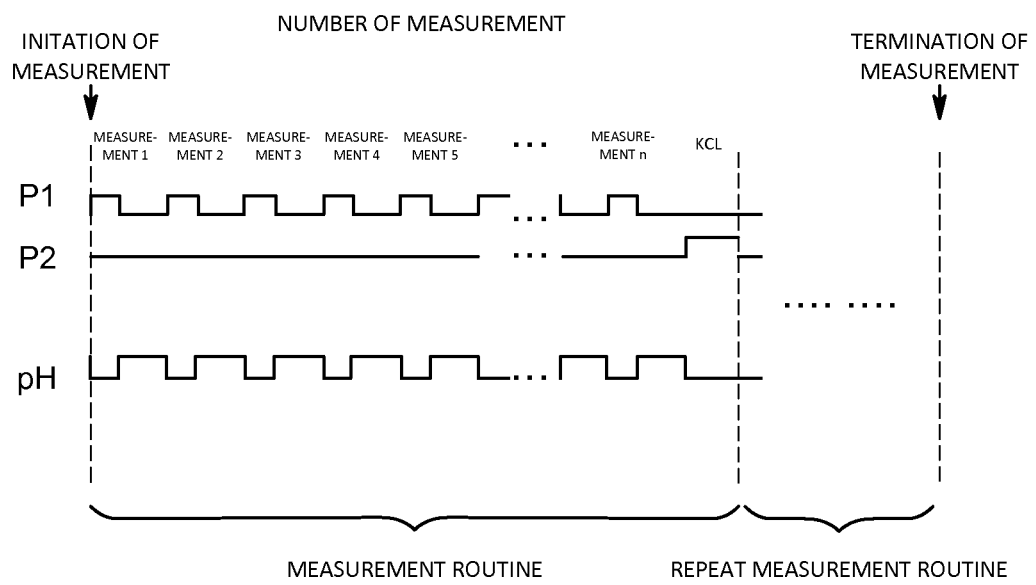
FIG. 3 is a schematic view showing a pH measurement sequence in accordance with one embodiment of this invention.

Next, a measuring sequence of the pH measurement of the measuring liquid 9 by using this measuring system 100 will be explained by the use of FIG. 3. A line of P1 indicates ON and OFF of the operation of the flow pump 10. Similarly, P2 indicates ON and OFF of the replenishing pump 18.

After correction of the measuring electrode 4 and the reference electrode 6 is conducted (not shown in drawings), the measurement is initiated. First, a measurement 1 will be explained. During the measurement 1, the flow pump 10 (P1) of the internal liquid replenishing mechanism 5 is operated during a predetermined period of time by the information processing/control mechanism 19 to flow the measuring liquid 9 in the flow-in pipe 12a and the flow-out pipe 12b so as to flow the measuring liquid 9 into the measuring electrode 4 and the reference electrode 6. An amount of the measuring liquid 9 introduced at this time is, for example, about several hundred µL. After the measuring liquid 9 flows in the measuring electrode 4 and the reference electrode 6, the flow pump 10 is once halted. At this time, the pH is measured.

As mentioned above, a process of operating and halting the flow pump 10 and of measuring the pH in the measurement 1 is considered to be one time measurement and this process is repeated at "n" times, namely the measurement of the pH is conducted by continuously repeating the process at, for example, 50 to 200 times. After the pH is measured, the flow pump 10 is halted by the information processing/control mechanism 19 and then the replenishing pump 18 (P2) is operated for a predetermined period of time so that the second internal liquid 15 such as a KCL solution or the like is replenished from the container 16 to the second internal liquid chamber 36 of the reference electrode 6 by a predetermined amount. The replenishing amount of the second internal liquid is an amount that can replace a part where the concentration of the second internal liquid 15 is diluted because the measuring liquid 9 flows in from the liquid junction 40 in the reference electrode 6. For example, about several tens µL of the second internal liquid is replenished.

"N" times of the measurement and the replenishment of the second internal liquid 15 are set to be one measurement routine, and the second internal liquid 15 is replenished periodically by repeating this measurement routine. After completion of the measurement routine that is repeated at a desired number of times, the pH measurement is terminated.

Since the measuring electrode 4 has an above-mentioned arrangement, it is possible to measure the electrical potential by flowing the measuring liquid 9 in the capillary shaped flow tube 58, resulting in reducing the amount of the measuring liquid 9 used for the measurement. With this arrangement, it is possible to decrease an amount of the chemical liquid that is discarded after the measurement. Especially, in case that the electric potential is measured when the flow of the measuring liquid 9 is halted by halting the flow pump 10, it is possible to further decrease the used amount of the chemical liquid.

In addition, even though a case that a temperature of the measuring liquid 9 is high, for example, about 50° C., since the temperature of the measuring liquid 9 drops while the measuring liquid 9 flows in the flow tube 58, no convection current occurs in the flow tube 58 even though the flow pump 10 is halted. As a result of this, it is possible to prevent dispersion of the measured electric potential due to the convection current so that the accuracy of the electric potential measurement can be improved. In addition, since the flow pump 10 is halted, the pH is measured by the measuring electrode 4 and the reference electrode 6 in a state that the flow of the chemical liquid is stopped. As a result of this, it is possible to avoid the influence on the pH value due to the flow of the chemical liquid.

In addition, in this embodiment, since the flow tube 58 is arranged above the upper end part of the internal electrode (M) and to pass a part of the first internal liquid chamber 52 having the constant cross section, air bubbles generated around the flow tube 58 due to the pH measurement do not attach to the flow tube 58 and are collected in the upper part of the first internal liquid chamber 52. With this arrangement, it is possible to prevent degradation of the measurement accuracy due to the air bubbles. In this embodiment, the upper end part of the first internal liquid chamber 52 is formed in a conical shape wherein the upper, the more the cross section decreases, however, it is not limited to this. The upper surface of the first internal liquid chamber 52 may be in a flat shape or a hemisphere as long as a space to hold the air bubbles is formed above the flow tube 58.

In addition, since the responsive glass of the flow tube 58 is made of a material containing a predetermined amount of Scandium, it has a hydrofluoric acid resistance. As a result of this, since it is difficult to be eroded even though the chemical solution to be measured is strong acidity containing hydrofluoric acid, the flow tube 58 can be used for a long period of time.

In addition, since the reference electrode 6 has the above-mentioned arrangement, it is possible to replenish the second internal liquid 15 from the replenishing port 17 locating below the upper end part of the internal electrode (R) and to replace the liquid around the internal electrode (R) with the second internal liquid 15 so that the measurement accuracy can be maintained. In this case, since the part of the second internal liquid 15 diluted by the measuring liquid 9 that flows in from the liquid junction 40 is pushed up and replaced by the second internal liquid 15, only the amount of the second internal liquid 15 corresponding to the diluted amount is required to be replenished so that it is possible to economize and reduce the replenishing amount of the second internal liquid 15.

The position of the replenishing port 17 may be appropriately varied. The replenishing port 17 may locate at a further downward position, in other words, at a bottom end part of the second internal liquid chamber 36. In this case, even though a case that a specific gravity of the second internal liquid 15 is smaller than that of the measuring liquid 9, since the replenishing port 17 locates at a position farthest from the liquid junction 40, the replenished second internal liquid 15 will not flow out from the liquid junction 40 and it is possible to replace the liquid around the internal electrode (R) securely with the amount of the second internal liquid 15 corresponding to the amount diluted by the measuring liquid 9 that flows in from the liquid junction 40 so that the replenishing amount of the second internal liquid 15 can be economized.

In addition, in case that the specific gravity of the second internal liquid 15 is bigger than that of the measuring liquid 9, the replenishing port 17 may locate above the upper end part of the internal electrode (R). In this case, since the specific gravity of the second internal liquid 15 is bigger than that of the measuring liquid 9, an amount of the second internal liquid 15 that flows out to a side of the measuring liquid 9 through the liquid junction 40 immediately after the second internal liquid 15 is replenished is small and the second internal liquid 15 remains around the internal electrode (R) due to its own weight. As a result of this, it is possible to keep the concentration of the second internal liquid 15 around the internal electrode (R). Furthermore, since the second internal liquid 15 whose specific gravity is bigger than the measuring liquid 9 is replenished, the part of the second internal liquid 15 diluted by the measuring liquid 9 that flows in from the liquid junction 40 can be pushed up securely so that it is possible to replace the liquid around the internal electrode (R) with the second internal liquid 15. Since it is possible to make the replenishing amount of the second internal liquid 15 correspond to part of the second internal liquid 15 diluted by the measuring liquid 9 that flows in from the liquid junction 40, the replenishing amount of the second internal liquid 15 can be economized and reduced.

In addition, since the internal electrode (R) is arranged to extend upward from the bottom end part of the second internal liquid chamber 36, even though the second internal liquid 15 is replenished intermittently by the replenishing pump 18 of the internal liquid replenishing mechanism 5 like the above-mentioned measurement sequence, the concentration of the liquid around the internal electrode (R) can be kept by making it possible to replace the second internal liquid 15 in time before the diluted part in the upper part of the second internal liquid chamber 36 reaches the internal electrode (R). As mentioned, since the second internal liquid 15 can be replenished intermittently, it is possible to reduce the replenishing amount of the second internal liquid 15 to the container 16 and to continuously operate this measuring system 100 without replenishing the second internal liquid 15 for a long period of time, for example, for 4 months to 8 months.

Although it is also possible to operate the replenishing pump 18 to flow an extremely subtle amount of the second internal liquid 15 without completely stopping the replenishing pup 18 so as to replenish the second internal liquid 15 by the amount that corresponds to the diluted amount due to the measuring liquid 9 that flows in at predetermined time intervals, it is preferable to completely halt the replenishing pump 18 during the pH measurement.

Furthermore, since the cross section in the predetermined distance (L1) from the liquid junction 40 is smaller than the cross section of the lower part than the predetermined distance (L1), the part in the predetermined distance (L1) becomes thinner than the part locating the internal electrode (R) so that it is possible to further reduce the amount of the part where the second internal liquid 15 is diluted by the measuring liquid 9 that flows in from the liquid junction 40. As a result of this, the amount of the part of the second internal liquid 15 to be replaced becomes less so that it is possible to further reduce the replenishing amount of the second internal liquid 15.

In addition, the predetermined distance (L1) is variously varied depending on the measurement condition. For example, a volume of the part where the second internal liquid 15 is diluted because the measuring liquid 9 flows in from the liquid junction 40 after conducting the pH measurement for a predetermined period of time is set to be (V2), and a distance from the liquid junction 40 is set to be (L2). And a volume in the second internal liquid chamber 36 to the predetermined distance (L1) is set to be (V1), (V1) and (L1) are so set to satisfy the relations of (V2)<(V1) and (L2)<(L1).

The amount of the second internal liquid 15 to be replenished is determined based on thus determined predetermined distance (L1) and its volume (V1). In this case, if the relation of (V2)<(V3)<(V1) holds between the amount to be replenished (V3) and the distance from the liquid junction 40 (L3), the relation of (L2)<(L3)<(L1) is established. Then it is possible to replace the part diluted by the measuring liquid 9 with the second internal liquid 15.

Furthermore, if the replenishing amount (V3) is an amount wherein the relation of (V2)<(V1)<(V3) is satisfied, the relation of (L2)<(L1)<(L3) is established so that the part diluted by the measuring liquid 9 can be sufficiently replaced with the second internal liquid 15. More specifically, in case that the second internal liquid 15 is diluted because the measuring liquid 9 diffuses in a space between the liquid junction 40 and the predetermined distance (L1), since an amount of the second internal liquid 15 more than the amount corresponding to the diluted amount is replenished, it is possible to push out the diluted part from the liquid junction 40 and to replace the diluted part with the second internal liquid 15 securely.

The volume (V2) of the diluted part and the replenishing amount (V3) of the second internal liquid 15 may satisfy at least a relation of (V2)<(V3).

Second Embodiment

Next, a second embodiment of this invention will be explained by the use of FIG. 4. The numerical codes in FIG. 4 that are the same as those in FIG. 2 indicate the same or corresponding configuration as that of the above-mentioned embodiment.

Figure 4:
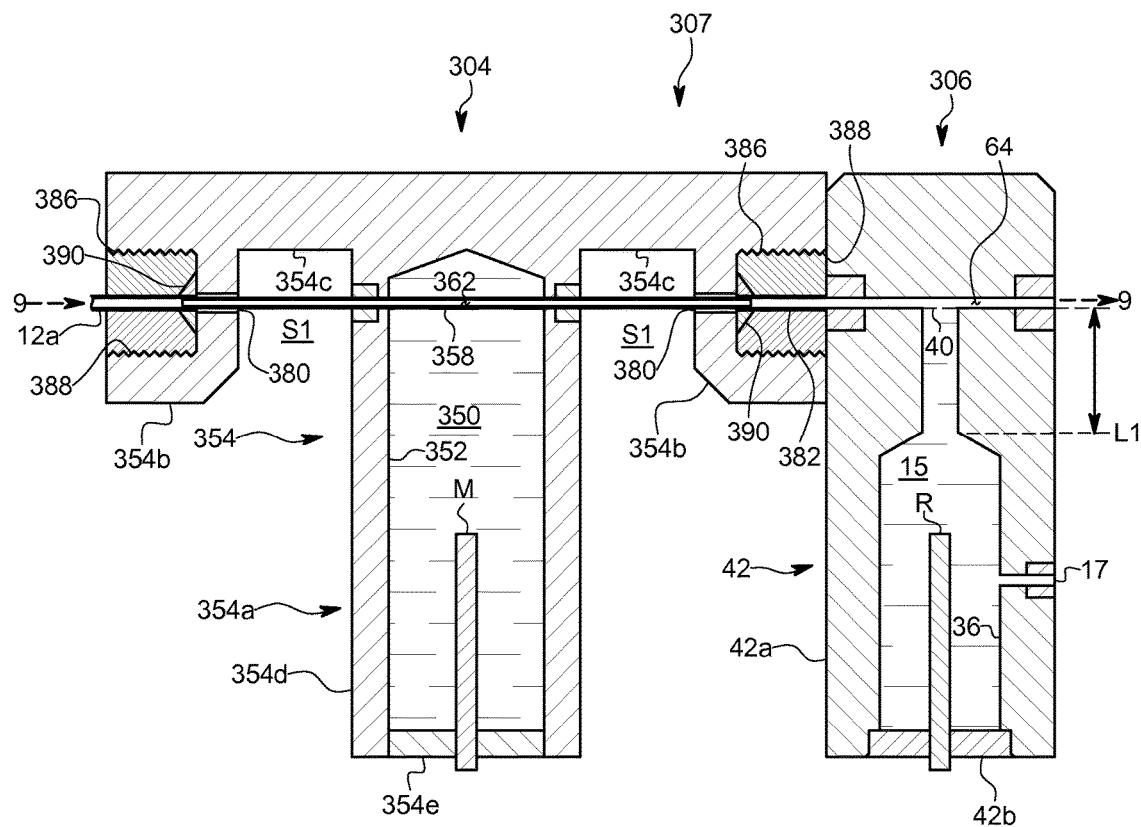
FIG. 4 is a schematic view of an electrode device in accordance with another embodiment of this invention.

The electrode device 307 comprises the measuring electrode 304 and the reference electrode 306 as shown in FIG. 4.

The measuring electrode 304 comprises a first body 354a having a first internal liquid chamber 352 into which a first internal liquid 350 is filled, a sub-body 354b arranged separately from the first body 354a and a connecting body 354c that connects the first body 354a and the sub-body 354b. Furthermore, the measuring electrode 304 comprises an internal electrode (M) mounted to extend upward from a bottom part of the first body 354a in the first internal liquid chamber 352. A body 354 of the measuring electrode 304 comprises the first body 354a, the sub-body 354b and the connecting body 354c. A material of the body 354 is the same as that of the above-mentioned first body 54. Similar to the first body 54, the first body 354a comprises a main member 354d and a cap body 354e, and a first internal liquid chamber 352 is formed inside of the main member 354d.

The sub-body 354b is a block body generally in a cuboid shape, and arranged separately from the first body 354a by a predetermined distance by integrally connecting an upper end part of one side surface of the first body 354a and an upper end part of one side surface of the sub-body 354b by the connecting body 354c whose shape is a generally cuboid shape. A space (S1) is formed between the first body 354a and the sub-body 354b each of which is arranged separately with its bottom part open. In this embodiment, similar to the above-mentioned sub-body 354b, another sub-body 354b is arranged separately from the first body 354a by integrally connecting an upper end part of the other side surface of the first body 354a and an upper end part of one side surface of the sub-body 354b by the connecting body 354c. Since each body is connected, the measuring electrode 304 is formed generally in a "T" character shape in a front view wherein the first body 354a locates in the center and the sub-body 354b is provided in each side through the connecting body 354c.

Furthermore, the sub-body 354b is provided with a female screw hole 388 as a connecting port with the reference electrode 306 and a male screw member 386 is arranged as being a fitting member to be screwed retractably and fittingly inserted into the female screw hole 388. Furthermore, the female screw hole 388 and the space (S1) are connected by a communicating hole 380.

Furthermore, in this embodiment, the measuring electrode 304 comprises a flow tube 358 where the measuring liquid 9 flows.

Whole of the flow tube 358 is formed by a responsive glass that responds a hydrogen ion and forms a first flow channel 362 where the measuring liquid 9 flows. A downstream side of the first flow channel 362 becomes an output end side of the flow tube 358 and an upstream side of the first flow channel 362 becomes an input end side of the flow tube 358. The material and the shape of the flow tube 358 are the same as those of the flow tube 58 in the first embodiment. In addition, similar to the flow tube 58 that is arranged in the first body 54, the flow tube 358 is arranged in the first body 354a.

Furthermore, the output end side of the flow tube 358 projects from the first body 354a so as to be inserted into the communicating hole 380 of the sub-body 354b. With this arrangement, a part of the flow tube 358 bridges the space (S1) arranged between the first body 354a and the sub-body 354b and the part of the flow tube 358 is exposed to the space (S1).

In addition, in this embodiment, the input end side of the flow tube 358 also projects from the first body 354a and the input end side is inserted into the communicating hole 380 formed on the sub-body 354b separately arranged from the other side surface of the above-mentioned first body 354a.

The responsive glass may be used for a part of the flow tube 358 that is immersed in the first internal liquid 350.

A configuration of the reference electrode 306 is the same as that of the reference electrode 6 in the above-mentioned embodiment.

Next, a concrete configuration of the electrode device 307 will be explained. The electrode device 307 is so configured that the flow tube 358 and a second flow channel 64 of the reference electrode 306 are connected by a connecting pipe 382 so that the measuring liquid 9 is supplied to the reference electrode 306 from the measuring electrode 304.

Concretely, one end side of the connecting pipe 382 is tightly connected to the second flow channel 64 by means of adhesive or the like and the other end side of the connecting pipe 382 fits over the output end side of the flow tube 358 so that a flow channel where the measuring liquid 9 flow is formed. Furthermore, a ring-shape member 390 to push a periphery of the connecting pipe 382 is arranged on an outer fitting part of the connecting pipe 382. More concretely, the ring-shape member 390 is a ring-member such as a ferrule having a tapered surface, and the male screw member 386 makes an abutting contact with the tapered surface by screwing the male screw member 386 into the female screw hole 388 so that the outer fitting part of the connecting pipe 382 is pushed by the ferrule and the connecting pipe 382 is fixed to the flow tube 358.

A distal end part of an inflow pipe 12a is connected to the input end side of the flow tube 358 so as to make the measuring liquid 9 flow in the flow tube 358 from the inflow pipe 12a. For example, the distal end part of the inflow pipe 12a fits over the input end side of the flow tube 358 and similar to the above-mentioned embodiment, a tightening member is arranged at this part so that the inflow pipe 12a is fixed to the flow tube 358.

In addition, the part of the first body 354a where the flow tube 358 penetrates is fixed to the flow tube 358 by means of adhesive or the like and sealed so as not to leak the first internal liquid 350 from the first internal liquid chamber 352.

Since the electrode device 307 has the above-mentioned configuration, even though the first internal liquid 350 leaks from the part of the first body 354a where the flow tube 358 penetrates due to the aged deterioration, the first internal liquid 350 is prevented from being transmitted to the reference electrode 306 by a space exposed area arranged in the output end side of the flow tube 358. As a result of this, it is possible to prevent the first internal liquid 350 of the measuring electrode 304 from mixing into the second flow channel 64 where the measuring liquid 9 flows in the reference electrode 306 securely. Since the bigger the space exposed area is, the more securely the first internal liquid is prevented from being transmitted to the reference electrode 306, it is preferable that the predetermined length of the projecting part is longer.

In addition, since the measuring electrode 304 comprises the sub-bodies 354b in addition to the first body 354a, it is possible to hold the projecting part of the flow tube 358 by the sub-bodies 354b.

Furthermore, in case that the sub-body 354b is connected to the first body 354a by the connecting body 354c, the first body 354a, the sub-body 354b and the connecting body 354c are integrally formed. As a result of this, the projecting part of the flow tube 358 can be held by the sub-body 354b more stably so that it is possible to prevent the flow tube 358 from being broken or cracked due to a contingent bending stress applied to the flow tube 358.

In addition, a distance between the first body 354a and the sub-body 354b is determined by a width of the connecting body 354c that connects the first body 354a and the sub-body 354b. The distance can be elongated by increasing the width of the connecting body 354c. With this arrangement, it is possible to make the first internal liquid 350 insulated from the reference electrode 306 securely. For example, in case that it is assumed to be that the leakage of the first internal liquid 350 becomes much, this arrangement is preferable.

Furthermore, a female screw hole 388 is arranged as a connecting port between the reference electrode 306 and the second flow channel 64 in a side of the sub-body 354b that contacts the reference electrode 306. With this arrangement, it is possible to supply the measuring liquid 9 to the second flow channel 64 securely by tightly connecting the flow tube 385 with the connecting pipe 382.

In addition, the reference electrode 306 may comprise a second sub-body and a second connecting body so as to make it possible to hold the projecting part of the flow tube 358. Concretely, the block shaped second sub-body is formed on a side surface of the reference electrode 306 to face the measuring electrode 304 through the second connecting body. As mentioned, a space similar to the above-mentioned space (S1) is formed by arranging the second sub-body separately from the second body 42. The flow tube 358 projecting from the first body 354a is held by the second sub-body and a part of the flow tube 358 bridges over the space.

In accordance with this arrangement, since the second body is formed on the second body 42 of the reference electrode 306 through the second connecting body, it is possible to hold the flow tube 358 without being broken. In addition, since a part of the flow tube 358 bridges over the space formed by the second body 42 and the second connecting body, the space exposed area is provided for the flow tube 358 so that the first internal liquid 350 is blocked from being transmitted to the reference electrode 306.

Third Embodiment

Next, a third embodiment will be explained by the use of FIG. 5.

Figure 5:
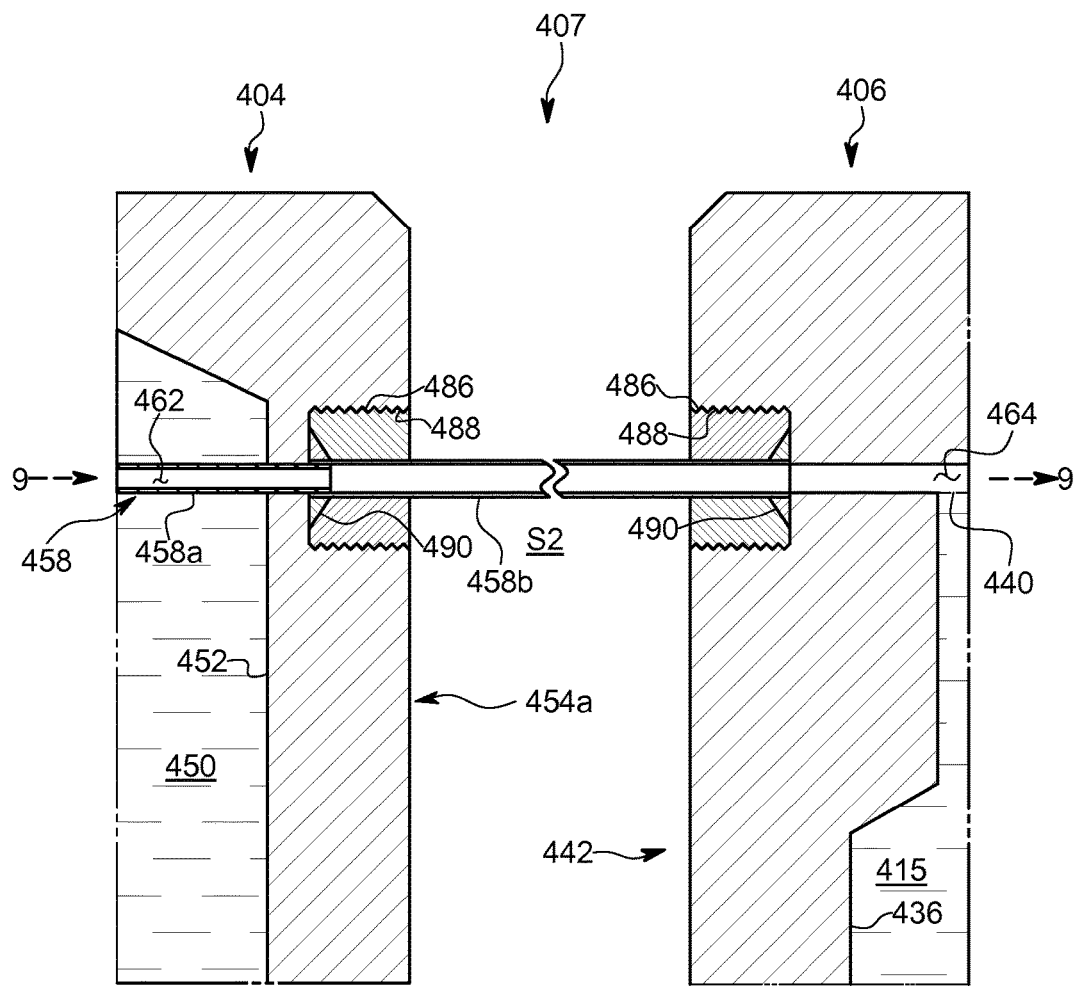
FIG. 5 is a partial enlarged view of an electrode device in accordance with a further different embodiment of this invention.
Figure 6:
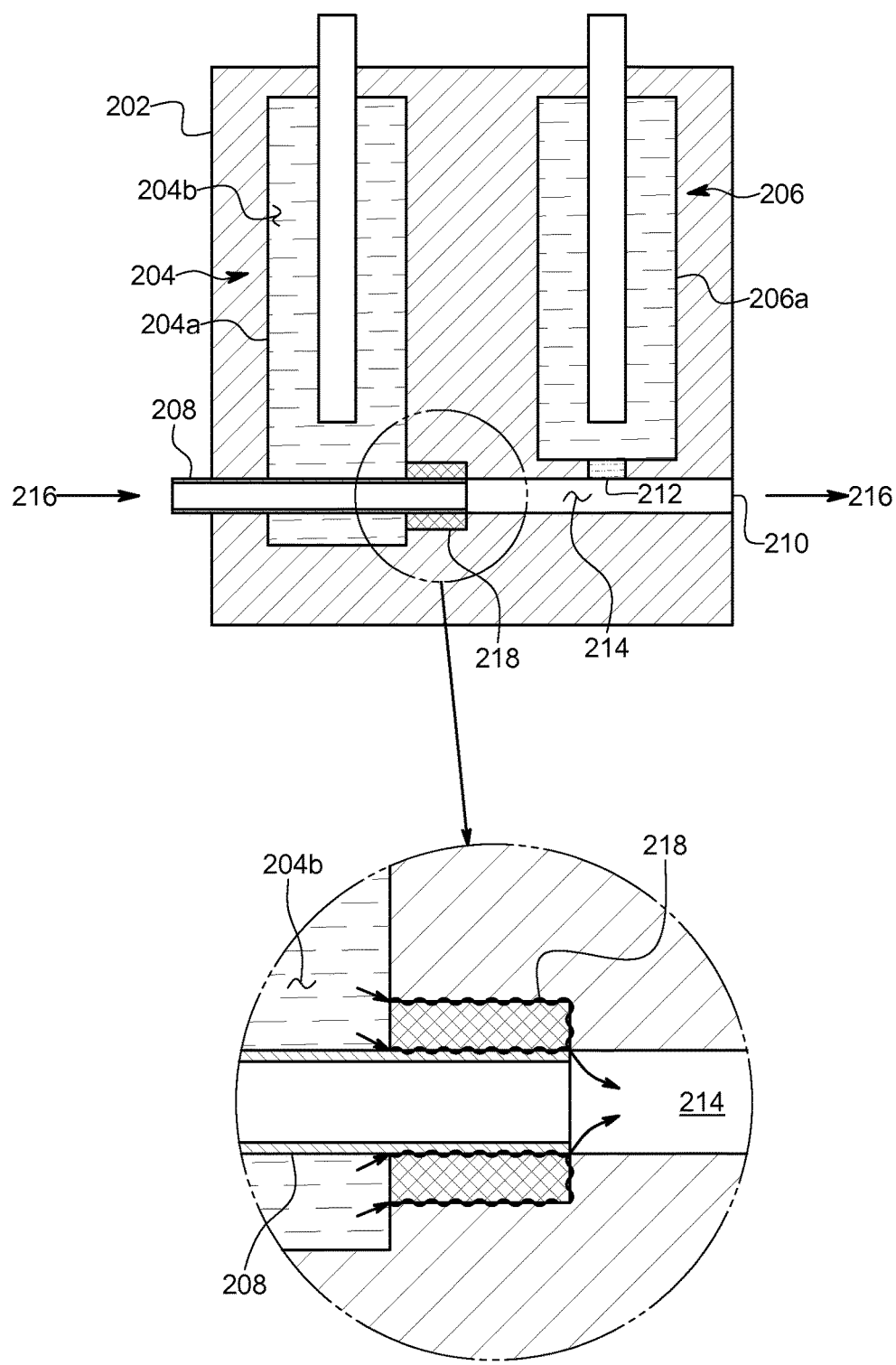
FIG. 6 is a schematic view of an electrode device in accordance with a further different embodiment of this invention.

The electrode device 407 comprises a measuring electrode 404 and a reference electrode 406 as shown in FIG. 5.

Whole of the flow tube 358 of the electrode device 307 in the above-mentioned embodiment is formed by the responsive glass. A flow tube 458 of the electrode device 407 is formed by a plurality of flow tube elements, each of which is connected, and each of the flow tube elements comprises a responsive glass tube 458a whole of which is formed by the responsive glass and an elastic tube 458b made of resin.

More specifically, a part of the flow tube 458 is made of the responsive glass. An output end side (one end side of the elastic tube 458b) of the flow tube 458 is connected to a second flow channel 464 of the reference electrode 406 so that the measuring liquid 9 is supplied to the reference electrode 406 from the measuring electrode 404. In addition, the reference electrode 406 is so configured that the second body 442 has a second internal liquid chamber 436 into which a second internal liquid 415 is filled and the second internal liquid 415 makes contact with the measuring liquid 9 that flows in the second flow channel 464 through a liquid junction 440.

Concretely, the other end part of the elastic tube 458b fits over one end part of the responsive glass tube 458a and the part where the elastic tube 458b fits over the responsive glass tube 458a is provided with a ring-shape tightening member 490 that presses down the part. More concretely, the tightening member 490 is, for example, a conical ferrule having a tapered surface, and a male screw member 486 is screwed into a female screw hole 488 formed on the first body 454a in a state that the male screw member 486 makes an abutting contact with the tapered surface. With this arrangement, the male screw member 488 presses the ferrule so as to be in a state that the male screw member 488 engages with the ferrule, and the part where the elastic tube 458b fits over the responsive glass tube 458a is pressed by the ferrule so that the responsive glass tube 458a and the elastic tube 458b are connected.

Since the elastic tube 458b has an elastic force, when the elastic tube 458b is pressed by the ferrule, the elastic tube 458b tightly attaches the responsive glass tube 458a that is made of a hard responsive glass so that the responsive glass tube 458a and the elastic tube 458b are liquid-tightly connected.

In addition, the output end side (one end side of the elastic tube 458b) of the flow tube 458 is also connected to the second flow channel 464 by the use of the tightening member 490.

Furthermore, a space (S2) is formed between the measuring electrode 404 and the reference electrode 406 arranged separately from the measuring electrode 404. In case of setting the measuring electrode 404 and the reference electrode 406 in the measuring system 300, even though the position of setting the measuring electrode 404 and the reference electrode 406 is misaligned, it is possible to absorb the positional displacement by the elastic tube 458b that is soft so that assembling the electrode device 407 becomes easy.

Since the electrode device 407 has the above-mentioned configuration, similar to the electrode device 307, it is possible to prevent the first internal liquid 450 filled in the first internal liquid chamber 452 from mixing into the first flow channel 462 as being a flow channel of the measuring liquid 9 so that an accuracy of measuring the electric potential can be kept.

The tightening member 490 may not be used, and the responsive glass pipe 458a and the elastic tube 458b may be connected by tightly attaching one end part of the responsive glass pipe 458a projecting from the first body 454a to the other end part of the elastic tube 458b by adhesive or the like. Furthermore, the output end side of the flow tube 458 also may be connected with the second flow channel 464 in a tightly attached state by the adhesive or the like.

Instead of the elastic tube 458b, a hard pipe may be connected to the responsive glass pipe 458a to constitute the flow tube 458 and the space (S2) is formed.

Furthermore, similar to the measuring electrode 304, the measuring electrode 404 or the reference electrode 406 may comprise the sub-body and the connecting body so as to form the space (S2) to hold the flow tube 458.

For example, in case of measuring not only the concentration of hydrogen but also the concentration of, for example, a sodium ion or a potassium ion simultaneously, a plurality of measuring electrodes may be arranged in parallel tailored to a kind of the ions to be measured so that the chemical liquid flowing out from the measuring electrode is merged and the reference electrode may be used in common. Alternatively, a plurality of measuring electrodes may be arranged in serial to measure the hydrogen ion, the sodium ion and the potassium ion in order and the reference electrode may be arranged further in serial and the reference electrode may be used in common. In accordance with this arrangement, it is possible to downsize the measuring system and to measure a plurality of ionic concentrations simultaneously.

In addition, as the measuring liquid as being the object to be measured is not limited to the chemical liquid used in the semiconductor manufacturing process. For example, since most of chemical liquids or material solutions used for food manufacture, medicine manufacture, medical equipment and cell culture is expensive with a small amount, the effect of this invention that the sample amount necessary to measure is small is especially remarkable. It is possible to apply this invention also to a general waste water treatment, a general water treatment, an industrial waste water treatment, an industrial water treatment, electric power generation, an automotive industry, an electric apparatus industry, a petrochemical industry, a metalworking industry, a resin processing industry, an environmental water quality analysis and a chemical plant.

In addition, this invention is not limited to the above-mentioned embodiments, and may be variously modified without departing from a spirit of the invention and a part or all of the above-mentioned embodiments or the modified embodiment may be appropriately combined.

EXPLANATION OF CODES

100 . . . measuring system
4, 304, 404 . . . measuring electrode
6, 306, 406 . . . reference electrode
7, 307, 407 . . . electrode device
10 . . . flow pump
17 . . . replenishing port
18 . . . replenishing pump
36 . . . second internal liquid chamber
40 . . . liquid junction
42 . . . second body
52 . . . first internal liquid chamber
54 . . . first body

The invention claimed is:
1. An electrode device comprising:
a measuring electrode; and
a reference electrode,
wherein the measuring electrode includes:
    a first body having a first internal liquid chamber into which a first internal liquid is filled, and
    a flow tube for a part or all of which a responsive glass is used and that forms a flow channel where a chemical liquid as being a measuring object flows and that is inserted into the first body so as to pass the first internal liquid chamber,
    wherein the flow tube is arranged in the first body so as to make the responsive glass of the flow tube contact with the first internal liquid in the first internal liquid chamber,
wherein the chemical liquid that flows in the flow tube is supplied to the reference electrode, and
wherein an output end side of the flow tube connected to the reference electrode projects from the first body to form a projecting part, and an area of the projecting part that extends over a predetermined length is exposed to a space.

2. A measuring system comprising:
the electrode device described in claim 1, and
a chemical liquid flow control mechanism that flows the chemical liquid to the flow tube of the measuring electrode, wherein
the chemical liquid flow control mechanism halts a flow of the chemical liquid at a time of measuring the chemical liquid.

3. The electrode device described in claim 1, wherein the flow tube is in a capillary shape.

4. The measuring system described in claim 2, wherein the flow tube is in a capillary shape.

5. The electrode device described in claim 1, wherein the measuring electrode further includes a sub-body arranged separately from the first body and a part of the flow tube bridges the space arranged between the first body and the sub-body.

6. The electrode device described in claim 5, wherein the measuring electrode further includes a connecting body connecting the first body and the sub-body.

7. The electrode device described in claim 1, wherein the reference electrode includes a second body forming a second internal liquid chamber into which a second internal liquid is filled and a second flow channel where the chemical liquid flows, and is configured such that the chemical liquid in the second flow channel makes contact with the second internal liquid in the second internal liquid chamber through a liquid junction.

8. The electrode device described in claim 7, wherein the reference electrode further includes a second sub-body arranged separately from the second body, and a part of the flow tube bridges over the space arranged between the second body and the second sub-body.

9. The electrode device described in claim 8, wherein the reference electrode further includes a second connecting body connecting the second body and the second sub-body.

10. The electrode device described in claim 1, wherein the flow tube is composed of a plurality of flow tube elements connected to each other.

11. The electrode device described in claim 10, wherein the plurality of flow tube elements are connected to each other in a manner such that one end part of one flow tube element fits over one end part of the other flow tube element, and a part where the flow tube elements fit each other is tightened by a ring-shape tightening member.

12. The electrode device described in claim 11, further comprising a fitting member, wherein the fitting member makes an abutting contact with the tightening member and fits into the first body so that the tightening member presses the part where the flow tube elements fit each other.

13. The electrode device described in claim 12, wherein the tightening member is a ferrule.

14. The electrode device described in claim 1, wherein a part of the space is open.

15. The electrode device described in claim 1, which is used for measuring a chemical liquid used in a semiconductor process.

\* \* \* \* \*